United States Patent
Kroll et al.

(10) Patent No.: US 7,374,784 B2
(45) Date of Patent: May 20, 2008

(54) METHOD FOR PRODUCING TABLETS FROM PLANT EXTRACTS

(75) Inventors: Ulrike Kroll, Münster (DE); Willi Kuper, Gross-Rohrheim (DE)

(73) Assignee: Steigerwald Arzneimittelwerk GmbH, Darmstadt (DE)

( * ) Notice: Subject to any disclaimer, the term of this patent is extended or adjusted under 35 U.S.C. 154(b) by 437 days.

(21) Appl. No.: 10/250,547

(22) PCT Filed: Jul. 15, 2002

(86) PCT No.: PCT/DE02/02634

§ 371 (c)(1),
(2), (4) Date: Nov. 24, 2003

(87) PCT Pub. No.: WO03/026620

PCT Pub. Date: Apr. 3, 2003

(65) Prior Publication Data

US 2004/0067265 A1 Apr. 8, 2004

(30) Foreign Application Priority Data

Sep. 3, 2001 (DE) ................. 101 44 108

(51) Int. Cl.
*A61K 36/00* (2006.01)
*A61K 36/38* (2006.01)
(52) U.S. Cl. ..................... 424/725; 424/730
(58) Field of Classification Search ........... 424/730; 264/109

See application file for complete search history.

(56) References Cited

U.S. PATENT DOCUMENTS 6,680,072 B1 * 1/2004 Kuper et al. ............. 424/489

FOREIGN PATENT DOCUMENTS

| EP | 0 530 833 A | 3/1993 |
| WO | WO 99 32090 A | 7/1999 |
| WO | WO 00 30605 | 6/2000 |

* cited by examiner

*Primary Examiner*—Christopher R Tate
*Assistant Examiner*—Randall Winston
(74) *Attorney, Agent, or Firm*—Wood, Phillips, Katz, Clark & Mortimer

(57) ABSTRACT

In a method for the production of tablets from plant extracts such as St. John's wort extract with an extract content of 80%, the extract treated on a conveyor dryer is compacted after adding 1% of silicon dioxide, and a granulate with a defined particle size distribution and therefore a defined surface area is produced from the compactate. To achieve a high rate of decomposition and active agent release with a low adjuvant content and high extract content, a combination of blasting agents including sodium hydrogencarbonate and two other, lower-dosed blasting agents such as croscarmellose sodium and sodium carboxymethyl starch—among other adjuvants—is added. The method results in a tablet suitable for oral administration containing 900 mg of St. John's wort extract.

9 Claims, No Drawings

METHOD FOR PRODUCING TABLETS FROM PLANT EXTRACTS

This invention relates to a method for producing tablets from plant extracts, in particular, St. John's wort extract, in which a dry extract mixed with adjuvants is compacted and granulated and the extract compact ate particles are masked with moisture protecting, surface smoothing, and separating agents are pressed into tablets together with other adjuvants.

Drugs in tablet form made from plant extracts are characterized by a more targeted release and more accurate dosing of the pharmaceutically effective ingredients as compared to liquid forms of application, which permits improved therapy control.

However, the forms of application of drugs made from plant extracts known as yet are necessary because a high portion of adjuvants is required both for the production process as well as for fast release of the active ingredients, rendering the active ingredient portion that can be put into a tablet with a limited volume to be suitable for oral administration comparatively small.

Using the above-mentioned method known from DE 199 57 472 A1, a tablet sized for oral administration with a St. John's wort extract can be produced in which the extract portion amounts to 65% or about 600 mg; this is mainly achieved by coating homogeneously sized particles of the extract compact ate that was formed with a high content of adjuvants with titanium dioxide, talc, and highly dispersed silicon dioxide. Coating the granulate with the adjuvants mentioned last ensures protection against moisture required for good flow behavior, homogeneous mixing with other adjuvants and a smooth surface of the compact ate particles to keep the content of other adjuvants low during mixing and coating and to be able to put a high extract content into a single tablet. Another desirable increase of the extract content during tablet production is encountering segregation or prepressing problems, or yields cores that are sensitive to moisture or too solid. In addition, keeping to the specified times for tablet decomposition and active ingredient release into the body is difficult if the active ingredient content is increased any further.

The main problem of producing tablets that have an extract content as high as possible and an accordingly low adjuvant content therefore is to ensure faultless tabletting and fast release of the active pharmaceutical ingredients.

It is therefore the problem of this invention to provide a method that prevents tabletting problems caused by segregation or decomposition due to moisture and enables the production of a tablet formed of plant extracts whose extract content is considerably increased as compared to known solid forms of application of this type and which has good decomposition and release properties.

This problem is solved according to the invention by a method comprising the characteristics described in claim 1.

Other characteristics and embodiments of the invention are described in the subclaims.

According to a first characteristic, the inventive idea is that the extract that is preferably dried on a conveyor dryer is compacted, i.e. pressed, using highly dispersed silicon oxide that also acts as a separating agent. According to a second characteristic of the invention, the extract compact ate particles are bigger and thus have a reduced surface as compared to known methods to keep the adjuvant content required for masking the extract compact ate particles to protect them against moisture and to improve their pressing behavior and decomposition properties low. A predefined particle size distribution is set to reduce the overall surface area of the extract compact ate particles by passing these particles through a sieve and allowing only specific particle sizes in specific quantities to pass on to the subsequent tabletting process. In order to meet the fast decomposition requirements with a tablet containing a high dose of plant extracts and a small portion of adjuvants, an adjuvant combination of three disintegrants is added according to yet another characteristic of the invention, one of which consisting of sodium hydrogencarbonate and exceeding the portion of the two other disintegrants by a multiple.

The essence of the invention therefore is the combination of adding a low percentage of highly dispersed silicon dioxide as early as prior to compacting, reducing the overall surface area of the extract compact ate particles by a defined particle size distribution, and using sodium hydrogencarbonate in conjunction with two other, significantly lower dosed disintegrants.

It is this combination of characteristics that makes it possible to produce, without tabletting problems, a tablet of an acceptable size with a low adjuvant content and a high extract content of about 80% that decomposes sufficiently fast in the body and meets the requirements of fast release.

One aspect of the invention is that the reduced extract is dried in a vacuum on a conveyor dryer. The percentage of silicon dioxide intermixed with the dry extract is only 1%. The extract compact ate particles are masked in a known way with titanium dioxide and talc for moisture protection and surface smoothing.

According to another important characteristic of the invention, the surface area of the extract compact ate particles is reduced as compared to known methods, which in combination with the disintegrants used according to the invention ensure the aimed decomposition of the tablet with a high dosage of herbal active ingredients, and a particle size distribution is set wherein at least 99% are smaller than 1,000 μm, at least 90% are smaller than 710 μm, 40% to 80% are smaller than 500 μm, 30% to 60% are smaller than 250 μm, and a maximum of 40% are smaller than 125 μm. This particle size distribution defines a particle surface with which the adjuvant portion for coating the particles can be further reduced.

According to yet another characteristic of the invention, the combination of disintegrants for the specified particle size distribution/surface area of the extract compact ate particles contains 5% to 15% of sodium hydrogencarbonate and 0.5% to 5% each of croscarmellose sodium and sodium carboxymethyl starch. At the concentrations specified, other common disintegrants such as starch derivatives, cellulose compounds, or polyvinyl pyrrolidone may also be used in combination with sodium hydrogencarbonate. The desired decomposition times are only achieved by the synergic effect of the disintegrants used in the combination at the specified limited quantity in relation to the overall adjuvant quantity. According to the invention, dry compacting or fluidized-bed granulation steps can be included in the process.

A method for producing film tablets with St. John's wort as the active ingredient that exemplifies the invention is described in greater detail below.

A liquid extract of St. John's wort buds and flowers produced using an ethanol-water mixture is filtered and reduced by approx. 60% by drying under reduced pressure at 40° to 60° C. The reduced extract is then subjected to high-temperature treatment (15 seconds at 140° C.) to reduce germs and to gentle conveyor drying under reduced pressure at temperatures between 30° and 60° C.

In a subsequent step, 1% of highly dispersed silicon dioxide is added to the St. John's wort extract as an adjuvant for the following compacting step, and the extract particles are coated with the silicon dioxide in a mixing process. Finally the extract prepared in this way is mechanically pressed into a compact ate and comminuted in a blending drum. The mixture of compacted extract compact ate particles is, passed through a sieve and cruder particles are selected for further processing into tablets to reduce the overall surface area. The particle size distribution is set so that at least at least 99% are smaller than 1,000 μm, at least 90% smaller than 710 μm, 40% to 80% smaller than 500 μm, 30% to 50% smaller than 250 μm, and a maximum of 40% smaller than 125 μm. The resulting bulk density of the extract particles selected for further processing is in the range from 0.63 to 0.80 g/ml and a tap density of 0.73 to 0.85 g/ml.

The extract compact ate particles in the specified particle size distribution are masked with titanium dioxide, talc, and vegetable magnesium stearate and additionally coated with sodium hydrogencarbonate, croscarmellose sodium, and sodium carboxymethyl starch. Subsequently, the extract compact ate particles that were intermixed with the specified adjuvants are pressed into tablets with an overall weight of 1090 mg using a tablet press; the St. John's wort content in such tablet is 900 mg while the tablet dimensions (9.5 mm in width, 20.5 mm in length, and 6.6 mm in height) make it suitable for oral administration. The tablet cores are then coated with a primer and a color enamel.

The invention claimed is:

1. A method for producing tablets from plant extracts, the method comprising the steps of:
   a) mixing highly dispersed silicon dioxide with a dry plant extract to produce a mixture of silicon dioxide and the dry plant extract;
   b) mechanically pressing the mixture:
   c) passing the mixture through a sieve to produce compacted extract particles where at least 99% of the particles are smaller than 1,000 μm, at least 90% of the particles are smaller than 710 μm, 40% to 80% of the particles are smaller than 500 μm, 30% to 60% of the particles are smaller than 250 μm and a maximum of 40% of the particles are smaller than 125 μm
   d) covering the compacted extract particles with moisture-protecting adjuvants;
   e) adding to the compacted extract particles a combination of at least three disintegrants, wherein the combination comprises between 5% and 15% by total weight of the compacted extract particles sodium hydrogencarbonate; and
   f) pressing the particles of step (e) into tablets by a tablet press.

2. The method according to claim 1, wherein the percentage of silicon dioxide within said mixture prior to mechanically pressing is 1%.

3. The method according to claim 1, wherein a bulk density of the compacted extract particles is from 0.63 to 0.80 g/ml and a tap density of the compacted extract particles is from 0.73 to 0.85 g/ml.

4. The method according to claim 1, wherein the combination of disintegrants comprises croscarmellose sodium and sodium carboxymethyl starch.

5. The method according to claim 1, wherein the combination of disintegrants comprises starch glycolates, cellulose compounds, or polyvinyl pyrrolidones.

6. The method according to claim 1, wherein the plant extract is St. John's wort extract.

7. The method according to claim 1, wherein the dry plant extract is dried under reduced pressure at 40° C. to 60° C. prior to step (a).

8. The method according to claim 1, wherein the moisture-protecting adjuvants comprise talc and titanium dioxide.

9. The method according to any one of claims 1, 2, 3, 4, 5 and 6, wherein the moisture-protecting adjuvants comprise vegetable magnesium stearate.

* * * * *